(12) United States Patent
Umezawa et al.

(10) Patent No.: US 7,507,555 B2
(45) Date of Patent: Mar. 24, 2009

(54) PROBE FOR DETECTING AND QUANTIFYING LIPID SECOND MESSENGER AND METHOD OF DETECTING AND QUANTIFYING LIPID SECOND MESSENGER USING THE SAME

(75) Inventors: Yoshio Umezawa, Tokyo (JP); Moritoshi Sato, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 116 days.

(21) Appl. No.: 10/554,194

(22) PCT Filed: Mar. 15, 2004

(86) PCT No.: PCT/JP2004/003433

§ 371 (c)(1),
(2), (4) Date: Oct. 24, 2005

(87) PCT Pub. No.: WO2004/095024

PCT Pub. Date: Nov. 4, 2004

(65) Prior Publication Data
US 2006/0265764 A1    Nov. 23, 2006

(30) Foreign Application Priority Data
Apr. 24, 2003    (JP)    ............................. 2003-120253

(51) Int. Cl.
*C12N 9/12*    (2006.01)
*C12Q 1/48*    (2006.01)
*G01N 33/52*    (2006.01)

(52) U.S. Cl. ...................... 435/69.1; 435/69.7; 435/15; 435/194; 436/94; 436/501

(58) Field of Classification Search ....................... None
See application file for complete search history.

(56) References Cited

U.S. PATENT DOCUMENTS 6,596,499 B2 *   7/2003  Jalink ......................... 435/7.1

FOREIGN PATENT DOCUMENTS

WO    WO 02/44720 A2 *   6/2002

OTHER PUBLICATIONS

Sefferenick et al. , J. Bateriology, vol. 183, pp. 2405-2410, 2001.*
Sato et al., "Production of PtdInsP$_3$ at endomembranes is triggered by receptor endocytosis", *Nature Cell Biology*, vol. 5, No. 11, pp. 1016-1022, 2003.

* cited by examiner

*Primary Examiner*—Andrew D Kosar
*Assistant Examiner*—Kagnew H Gebreyesus
(74) *Attorney, Agent, or Firm*—Wenderoth, Lind & Ponack, L.L.P.

(57) ABSTRACT

The present invention provides probes for detection and quantification of a lipid second messenger, which comprises: a polypeptide specifically bound to the lipid second messenger; two chromophores respectively having different fluorescence wavelengths, wherein each of the chromophores is linked to each end of the polypeptide through a rigid linker sequence; and a membrane localization sequence linked to one of the chromophores through a rigid linker sequence. According to the present invention, it is now possible to quantitatively detect when and in which site of a living cell the lipid second messengers are produced.

8 Claims, 15 Drawing Sheets

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial
<220> FEATURE:
<223> OTHER INFORMATION: Description of artificial sequence:
      Synthetic oligopeptide

<400> SEQUENCE: 1

Glu Ala Ala Ala Arg
1               5

<210> SEQ ID NO 2
<211> LENGTH: 30
<212> TYPE: PRT
<213> ORGANISM: Artificial
<220> FEATURE:
<223> OTHER INFORMATION: Description of artificial sequence:
      Synthetic oligopeptide

<400> SEQUENCE: 2

Glu Ala Ala Ala Arg Glu Ala Ala Ala Arg Glu Ala Ala Ala Arg
1               5                   10                  15

Glu Ala Ala Ala Arg Glu Ala Ala Ala Arg Glu Ala Ala Ala Arg
                20                  25                  30

<210> SEQ ID NO 3
<211> LENGTH: 32
<212> TYPE: PRT
<213> ORGANISM: Artificial
<220> FEATURE:
<223> OTHER INFORMATION: Description of artificial sequence:
      Synthetic oligopeptide

<400> SEQUENCE: 3

Glu Ala Ala Ala Arg Glu Ala Ala Ala Arg Glu Ala Ala Ala Arg
1               5                   10                  15

Gly Gly Glu Ala Ala Ala Arg Glu Ala Ala Ala Arg Glu Ala Ala
                20                  25                  30

Ala Arg

<210> SEQ ID NO 4
<211> LENGTH: 35
<212> TYPE: PRT
<213> ORGANISM: Artificial
<220> FEATURE:
<223> OTHER INFORMATION: Description of artificial sequence:
      Synthetic oligopeptide

<400> SEQUENCE: 4

Glu Ala Ala Ala Arg Glu Ala Ala Ala Arg Glu Ala Ala Ala Arg
1               5                   10                  15
```

```
Glu Ala Ala Ala Arg Glu Ala Ala Ala Arg Glu Ala Ala Ala Arg
                 20                  25                  30
Glu Ala Ala Ala Arg
                 35

<210> SEQ ID NO 5
<211> LENGTH: 11
<212> TYPE: PRT
<213> ORGANISM: Artificial
<220> FEATURE:
<223> OTHER INFORMATION: Description of artificial sequence:
      Synthetic oligopeptide

<400> SEQUENCE: 5

Gln Gly Cys Met Gly Leu Pro Cys Val Val Met
1                5                  10

<210> SEQ ID NO 6
<211> LENGTH: 11
<212> TYPE: PRT
<213> ORGANISM: Artificial
<220> FEATURE:
<223> OTHER INFORMATION: Description of artificial sequence:
      Synthetic oligopeptide

<400> SEQUENCE: 6

Gln Gly Ser Met Gly Leu Pro Cys Val Val Met
1                5                  10
```

US 7,507,555 B2

PROBE FOR DETECTING AND QUANTIFYING LIPID SECOND MESSENGER AND METHOD OF DETECTING AND QUANTIFYING LIPID SECOND MESSENGER USING THE SAME

This application is a U.S. national stage of International Application No. PCT/JP2004/003433 filed Mar. 15, 2004.

TECHNICAL FIELD

The invention of the present application relates to a probe for detection and quantification of a lipid second messenger. More particularly, the invention of the present application relates to a probe for detection and quantification of a lipid second messenger for the quantitative detection of when and where the lipid second messenger is produced in living cells, and to a method for detecting and quantifying the lipid second messenger using the probe.

BACKGROUND ART

Phosphatidylinositol-3,4,5-trisphosphate ($PIP_3$), one of the lipid second messengers, is present in cell membranes and plays an important role in intracellular signal transduction. To be more specific, it has been known to activate its binding protein such as Akt, PDK1 and Btk, and to adjust various cell functions associated with apoptosis, diabetes mellitus, cancer, and so on (Cantley, L. C. (2002) *Science,* 296, 1655-1657; Czech, M. P. (2000) *Cell,* 100, 603-606; Vanhaesebroeck, B and Alessi, D. R. (2000) *Biochem. J.,* 346, 561-576). It has been clarified that production of $PIP_3$ in cell membranes is catalyzed by phosphatidylinositol-3-kinase (PI3K) (Wymann, M. P. and Pirola, L. (1998) *Biochim. Biophys. Acta,* 1436, 127-150). A large number of stimuli elicit the PI3K activation, however, exactly how, when, and where the $PIP_3$ production occurs has remained unknown. This appears to be due in part to the lack of appropriate methods to quantitatively analyze the spatial and temporal dynamics of $PIP_3$ in single living cells. Actually, labeling of cells with [$^{32}$P]orthophosphate has widely been used to measure $PIP_3$ changes, however, this method has several limitations to obtain such spatial and temporal information, because millions of cells must be smashed and analyzed to obtain sufficient radiochemical signals. Recently, fused proteins of green fluorescent protein (GFP) and $PIP_3$ binding domains derived from Btk (Varnal, P., Rother, K. I. and Balla, T. (1999) *J. Biol. Chem.,* 274, 10983-10989), GRP1 (Venkateswarlu, K., Gunn-Moore, F., Tavare, J. M. and Cullen, P. J. (1998) *Biochem. J.,* 335, 139-146), ARNO (Venkateswarlu, K., Oatey, P. B., Tavare, J. M. and Cullen, P. J. (1998) *Curr. Biol.,* 8, 463-466) or Akt (Watton, J. and Downward, J. (1999) *Curr. Biol.,* 433-436) have been reported as indicators for $PIP_3$ accumulation in the cellular membrane, in which the translocation of the fusion proteins from the cytosol to the membrane has been explained to reflect the $PIP_3$ accumulation. However, several factors such as changes in the cell shapes and membrane ruffles, which are frequently observed during fluorescence imaging experiments, cause serious artifacts. Moreover, it is difficult with these fluorescent fusion proteins to distinguish to which membranes the fusion proteins translocated in the cell.

The invention of the present application has been conducted in view of the above-mentioned circumstances and its object is to solve the problems in prior arts. The present invention aims to provide a probe for quantitatively detecting when and where lipid second messengers such as $PIP_3$ are produced in single living cells. The invention of the present application also provides a method for screening a substance which affects the signaling by an intracellular lipid second messenger and a diagnostic method by measuring the signal associated with the diseases by using the probe as such.

DISCLOSURE OF THE INVENTION

In order to solve the above problems, the invention of this application firstly provides a probe for detection and quantification of a lipid second messenger, which comprises:

a polypeptide specifically bound to the lipid second messenger, two chromophores respectively having different fluorescence wavelengths, wherein each of the chromophores is linked to each end of the polypeptide through a rigid linker sequence; and a membrane localization sequence linked to one of the chromophores through a rigid linker sequence.

Secondly, the invention of this application is the probe for detection and quantification of a lipid second messenger, wherein said polypeptide specifically bound to the lipid second messenger is a lipid second messenger-binding protein. Thirdly, it provides the probe for detection and quantification of a lipid second messenger, wherein said lipid second messenger-binding protein is a pleckstrin homology domain from GRP1.

Fourthly, the invention of this application provides the probe for detection and quantification of a lipid second messenger of any one of the above, wherein the chromophores are a cyan fluorescent protein linked to N-terminal end of the polypeptide and a yellow fluorescent protein linked to C-terminal end of the polypeptide.

Fifthly, the invention of this application provides the probe for detection and quantification of a lipid second messenger of any one of the above, wherein the linker sequence is a rigid α-helix linker consisting of repeated sequences of SEQ ID NO: 1. Sixthly, it provides the probe for detection and quantification of a lipid second messenger of any one of the above, wherein at least one linker sequence has a single di-glycine motif.

Seventhly, the invention of this application provides the probe for detection and quantification of a lipid second messenger of any one of the above, wherein the membrane localization sequence is a lipidized sequence or a transmembrane sequence.

Eighthly, the invention of this application provides a method for detecting and quantifying a lipid second messenger, which comprises:

co-existing the probe for detection and quantification of a lipid second messenger of any one the above with the lipid second messenger; and measuring changes in fluorescence spectra.

Ninthly, the invention of this application provides the method for detecting and quantifying a lipid second messenger, which comprises:

introducing a polynucleotide expressing the probe for detection and quantification of a lipid second messenger of any one of the above into cells; and co-existing the probe with the lipid second messenger.

Tenthly, it provides the method for detecting and quantifying a lipid second messenger, which comprises:

introducing a polynucleotide expressing the probe for detection and quantification of a lipid second messenger of any one of the above into a non-human totipotent cell; and ontogenizing the cell to non-human animal, thereby co-existing the probe with the lipid second messenger in all cells of the animal or offspring animal.

Eleventhly, the invention of the present application provides the method for detecting and quantifying a lipid second messenger according to any one of the above method, wherein the probe for detection and quantification of a lipid second messenger is tethered to a membrane in the cells, and the lipid second messenger produced in the membrane is detected and quantified.

Twelfthly, the invention of this application provides a non-human animal or offspring animal thereof, which is obtained by:

introducing a polynucleotide expressing the probe for detection and quantification of a lipid second messenger of any one of the above into a non-human totipotent cell; and ontogenizing the cell to the non-human animal.

Thirteenthly, the invention of this application provides a method for screening a substance for quantifying a lipid second messenger in the cells of the non-human animal or offspring animal thereof of the above which comprises introducing a test sample into the non-human animal or the offspring animal thereof.

Figure 1:
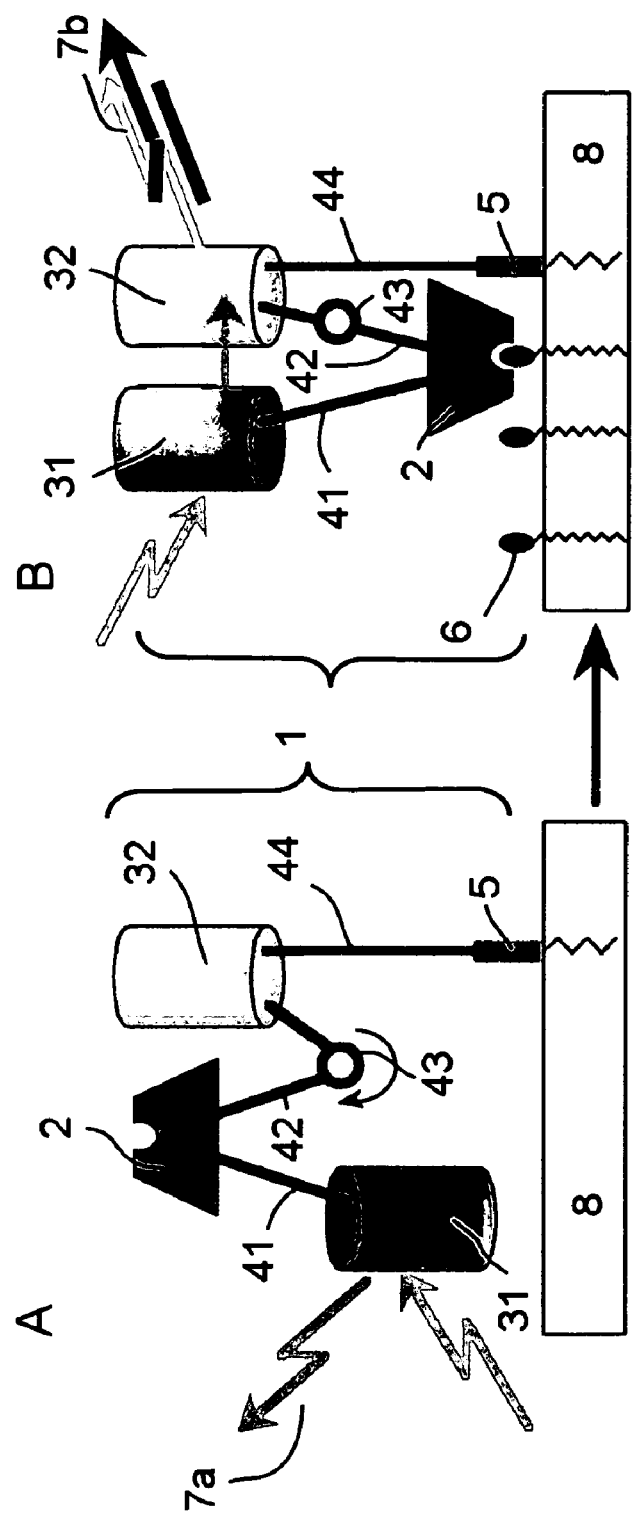
FIG. 1 is a principle of the lipid second messenger probe of the present invention.

symbols in the drawings mean as follows.

| | |
|---|---|
| A | Absence of lipid second messenger |
| B | Presence of lipid second messenger |
| 1 | A lipid second messenger detecting- and quantifying-probe |
| 2 | Specific binding site for lipid second messenger |
| 31 | chromophore (CFP) |
| 32 | chromophore (YFP) |
| 41 | rigid linker sequence |
| 42 | rigid linker sequence |
| 43 | flexible site |
| 44 | rigid linker sequence |
| 5 | membrane localization sequence |
| 6 | lipid second messenger |
| 7a | emission in the absence of lipid second messenger |
| 7b | emission in the presence of lipid second messenger |
| 8 | membrane |

BEST MODE FOR CARRYING OUT THE INVENTION

The probe for detection and quantification of a lipid second messenger according to the present invention comprises three sites having different functions, respectively. Thus, the probe for detection and quantification of a lipid second messenger comprises: a lipid second messenger-specific binding site, which specifically recognizes the lipid second messenger; a coloring site emitting optical signal upon recognition of a lipid second messenger at the specific binding site; and a membrane tethering site to tether the probe to the membrane.

FIG. 1 shows a schematic drawing of the probe for detection and quantification of a lipid second messenger according to the present invention. Probe 1 is based on a principle that, when probe 1 coexists with a lipid second messenger 6, the specific binding of lipid second messenger 6 with specific binding site 2 causes changes in configuration between chromophores 31 and 32, which then leads to changes in optical signals 7a and 7b. Measuring the signal changes 7a and 7b makes it possible to specify and quantify where and when the lipid second messenger is produced.

The lipid second messenger-specific binding site 2 is, for example, a polypeptide such as lipid second messenger-binding proteins. Preferable examples for the lipid secondary messenger-binding proteins include pleckstrin homology domain (hereinafter, referred to as PH domain) of GRP1 (Venkatewarlu, K., Gunn-Moore, F., Tavare, J. M. and Cullen, P. J. (1998) *Biochem. J.,* 335, 139-146), PH domain of ARNO, PH domain of Btk in the case of the lipid second messenger 6 being phosphatidylinositol-3,4,5-triphosphate ($PIP_3$); PH domain of TAPP for phosphatidylinositol-3, 4-diphosphate ($PI(3,4)P_2$); PH domain of PLCδ for phosphatidylinositol-4, 5-diphosphate ($PI(4,5)P_2$); PX domain of p40phox and FYVE domain of EEA1-2× for phosphatidylinositol-3-phosphate ($PI(3)P$) (Misra, S., Miller, G. J. and Hurley, J. H. (2001) *Cell,* 107, 559-562); C1 domain of PKC for diacylglycerol (Zhang, C., Kazanietz, M. G., Blumberg, P. M. and Hurley, J. H. (1995) *Cell,* 81, 917-924), etc.

The specific binding site 2 is not limited to the above, so far as it is a polypeptide specifically binding to the lipid second messenger 6, and all kinds of natural and synthetic peptides may be used.

In probe 1 of this invention, various chromophores 31 and 32 may be employed as the coloring sites. The chromophores 31 and 32 are required to change the wavelengths by precisely responding to a conformational change in probe 1 that is resulted upon binding of lipid second messenger 6 with specific binding site 2.

In the field of biochemistry, various fluorescent chromophores are usually used. As a chromophore capable of quickly responding to conformation changes, there is a chromophore that changes color tone by occurrence of fluorescence resonance energy transfer (FRET) (Miyawaki, A and Tsien, R. Y. (2000) *Method. Enzymol.,* 327, 472-500; Sato, M., Hida, N., Ozawa, T., and Umezawa, Y. (2000) *Anal. Chem.,* 72, 5918-5924; Sato, M., Ozawa, T., Inukai, K., Asano, T. and Umezawa, Y. (2002) *Nature Biotechnol.,* 20, 287-294).

Accordingly, in probe 1 of this invention, as a site for optical signal change resulted from recognition of the lipid second messenger molecule, each of two fluorescent chromophores 31 and 32 having different fluorescence wavelengths respectively is linked to both terminals of specific binding site 2. Examples of the fluorescent chromophores as such are cyan fluorescent protein (CFP), a blue shift variant protein of green fluorescent protein (GFP) and yellow fluorescent protein (YFP), a red shift variant protein of GFP. CFP 31 linked at N-terminal and YFP 32 at C-terminal of a lipid second messenger-specific binding polypeptide act as a donor and a acceptor, respectively, and FRET occurs. The chromophore is not limited to the above examples, various kinds thereof acting as donor/acceptor for FRET may be applied.

Probe 1 of this invention has a membrane localization sequence 5 at the terminal thereof for tethering itself at a membrane, since lipid second messenger 6 is produced in membrane 8 such as plasma membranes and endomembranes. Such membrane localization sequence 5 is linked to any of the chromophores and has a role of tethering probe 1 at membrane 8. To be more specific, for tethering the probe to cell membranes, a lipidizatoin sequence such as K-Ras and N-Ras (Resh, M. D. (1996) *Cell. Signal.,* 8, 403-412) and transmembrane sequence are exemplified. By appropriately selecting membrane localization sequence 5 depending upon lipid second messenger 6 to be detected or membrane 8 to be tethered, probe 1 is able to be tethered not only to plasma membranes or endomembranes but also to other organelle membranes such as inner membrane of nucleus or outer membrane of mitochondria. To be more specific, C181S variant of N-Ras for endoplasmic reticulum membrane and Golgi body membrane; Tom20 for mitochondrial membrane; caveolin for caveola; and Cbp for raft may be exemplified. In addition, lipid second messenger 6 on organelle membrane such as other nuclear membrane or peroxisome membrane may be detected by using a localization sequence of a protein localized in each organelle membrane.

When probe 1 of this invention is introduced into cells, probe 1 is tethered to cell membranes and has a conformation where two chromophores 31 and 32 are apart (A). When lipid second messenger 6 is produced in cell membrane 8, specific binding site 2 specifically recognizes and binds it, and conformational change of probe 1 occurs. As a result, the two chromophores 31 and 32 come closer to result in FRET (B).

For the purpose that FRET is resulted from such a mechanism and lipid second messenger 6 is detected as an optical change, it is necessary that the two fluorescence chromophores 31 and 32 having different fluorescence wavelengths in probe 1 are sterically parted in the absence of lipid second messenger 6, and that the conformation of probe 1 is quickly reversed upon binding of lipid second messenger 6 and specific binding site 2. Therefore, specific binding site 2 and fluorescence chromophores 31 and 32 are linked through a rigid linker sequences 41 and 42 such as a rigid α-helical linker comprising repeated sequences of EAAAR (SEQ ID NO: 1) (Merutka, G., Shalongo, W. and Stellwagen, E. (1991) *Biochemistry,* 30, 4245-4248).

Further, it is desired that at least one of the rigid linker sequences 41 and 42 have a flexible site 43 acting as a hinge. According to this structure, when probe 1 is tethered to the cell membrane 8, it shows the conformation where two chromophores 31 and 32 are apart in the absence of lipid second messenger 6. On the other hand, when lipid second messenger 6 is produced in the cell membrane 8, specific binding site 2 binds to lipid second messenger 6 and the conformation is reversed so that two chromophores 31 and 32 come closer. Hinge-like flexible site 43 may comprise several amino acids having small side chains, and its specific example includes a di-glycine motif.

In probe 1 of this invention, membrane localization sequence 5 and fluorescent chromophore 32 shall be also linked through the same rigid linker sequence 44. Although membrane localization sequence 5 may be linked to any of chromophores 31 and 32, for taking a preferred conformation when probe 1 is tethered to cell membrane 8, it is desired that membrane localization sequence 5 shall be linked to the chromophore 32 to which linker sequence 42 having hinge-like flexible site 43 is linked.

As mentioned above, when probe 1 of this invention coexists with lipid second messenger 6, specific binding site 2 binds to lipid second messenger 6 and FRET by fluorescence chromophores 31 and 32 at N- and C-terminals, respectively, occurs whereby fluorescence spectra are changed. Accordingly, when the fluorescence change is measured by commonly used various chemical or biochemical analytical methods, it is now possible to detect lipid second messenger 6. In addition, if the relation between the fluorescence intensities corresponding to some amounts of lipid second messenger 6 is previously calibrated, it is also possible to quantify the lipid second messenger in a sample.

In the invention of the present application, various methods are available for coexisting probe 1 with lipid second messenger 6. For example, cells are destructed, a lipid second messenger is extracted from the cells, and probe 1 is added to the solution thereby probe 1 and lipid second messenger 6 coexist. In this method, further, a lipid is previously supplied to form liposome membrane and probe 1 is localized on the liposome membrane thereby lipid second messenger 6 can be detected and quantified in vitro.

Further, in accordance with the invention of this application, it is also possible to coexist probe 1 with lipid second messenger 6 in cells by introducing an expression vector expressing probe 1 into each culture cell. With regard to the expression vector, plasmid vectors for animal cells are preferably used. Introduction of the plasmid vector into cells may be performed with known methods such as electroporation, calcium phosphate method, liposome method and DEAE dextran method. As above, employing the method for introducing probe 1 expression vector into cells, probe 1 and lipid second messenger 6 are able to coexist in cells. Accordingly, it is possible to conduct an in vivo detection and quantification of lipid second messenger 6 without destruction of cells.

Furthermore, in accordance with the method for detecting and quantifying a lipid second messenger of this invention, a polynucleotide expressing probe 1 is introduced into a non-human animal totipotent cell and then the cell is ontogenized into the non-human animal. Probe 1 coexists with lipid second messenger 6 within all cells of the animal or offspring animal thereof. In this case, probe 1 expressed in the cells is tethered to the membrane on cells and the lipid second messenger produced in the cells can be detected and quantified.

In the invention of the present application, the polynucleotide to express probe 1 can be introduced into the non-human totipotent cells by various methods as mentioned above, and probe 1 coexists with lipid second messenger 6 in the cells of the transgenic non-human animal. A transgenic non-human animal can be established by a known preparing method (such as *Proc. Natl. Acad. Sci. USA,* 77: 7380-7384, 1980). The transgenic non-human animal has probe 1 in all somatic cells and, therefore, when a test substance such as drug or toxin is introduced into its body and concentration of a lipid second messenger in cells and tissues is measured, it is now possible to screen various substances.

As hereunder, Examples according to the attached drawings will be shown to illustrate the invention in more detail. It goes without saying that the invention is not limited to the following Examples but various embodiments in particulars are possible.

EXAMPLES

[Preparations]

(1) Reagents

In the following Examples, each of materials and reagents used was as follows.

Synthetic $PIP_3$ and L-α-phosphatidyl-D-myo-inositol-3,4,5-triphosphate (Dic16) were purchased from Wako Pure Chemical (Osaka, Japan). Hamls F-12 medium, fetal calf serum, Hank's balanced salt solution and LipofectAMINE 2000 reagent were obtained from Life Technologies (Rockville, Md.). Dulbecco's modified Eagle medium and PDGF-BB were purchased from Sigma Chemical (St. Louis, Mo.). Anti-GFP antibody was obtained from Clontech (Palo Alto, Calif.). Anti-rabbit IgG antibody labeled with Cy5 was obtained from Jacson ImmunoResearch Lab., Inc. (West Glove, Pa.). BONIPY-ceramide CS and breferdin A were purchased from Molecular Probes Inc. (Eugene, Oreg.).

CFP mutations were F64L/S65T/Y66W/N146I/M 153T/V163A/N212K, and YFP mutation was S65G/V68L/Q69K/S72A/T203Y.

Other chemicals used were all of analytical reagent grade.

(2) Plasmid Construction

To construct cDNAs of a probe for detecting and quantifying a lipid second messenger, fragment cDNAs of CFP, PHD with linker sequences (Ln1 and Ln2), YFP with a linker sequence (Ln3) and membrane localization sequence (MLS 1), PHD-R284C (the 84th R in PHD was substituted with C) with linker sequences (Ln1 and Ln2), YFP with a linker sequence (Ln3) (hereinafter, referred to as "YFP-Ln3") and YFP with a linker sequence (Ln3) and a membrane localization sequence (MLS2) were generated by standard PCR.

Each cDNA was subcloned into pBLuescript SK(+). All cloning enzymes were from Takara Biomedical (Tokyo, Japan) and were used according to the manufacturer's instructions. All PCR fragments were sequenced with an ABI310 genetic analyzer. Each cDNA encoding the probes was subcloned at HindIII and XhoI sites of a mammalian expression vector, pcDNA3.1(+) (Invitrogen Co., Carlsbad, Calif.).

Example 1

Preparation of a Probe for Detection and Quantification of a Lipid Second Messenger As shown in FIG. 1, cyan fluorescence protein (CFP), a variant of green fluorescence protein (GFP) (for example, *Current Biology* 6(2): 178-182, 1996) derived from *Aequorea victoria* is linked by a genetic engineering techniques at N-terminal of PHD derived from human GRP1 (261-382) through the linker Ln1 (SEQ ID NO: 2), while yellow fluorescence protein (YFP) is similarly linked at C-terminal of the PHD through the linker Ln2 (SEQ ID NO: 3) and, further, a CAAX box motif of N-Ras (Choy, E. et al. (1999) *Cell*, 98, 68-80) is linked through the linker Ln3 (SEQ ID NO: 4) at C-terminal of YFP as the membrane localization sequence MLS1 (SEQ ID NO: 5). Thus, probe 1 for detection and quantification of a lipid second messenger (hereinafter, referred to as "Fllip-pm") was prepared.

Figure 2:
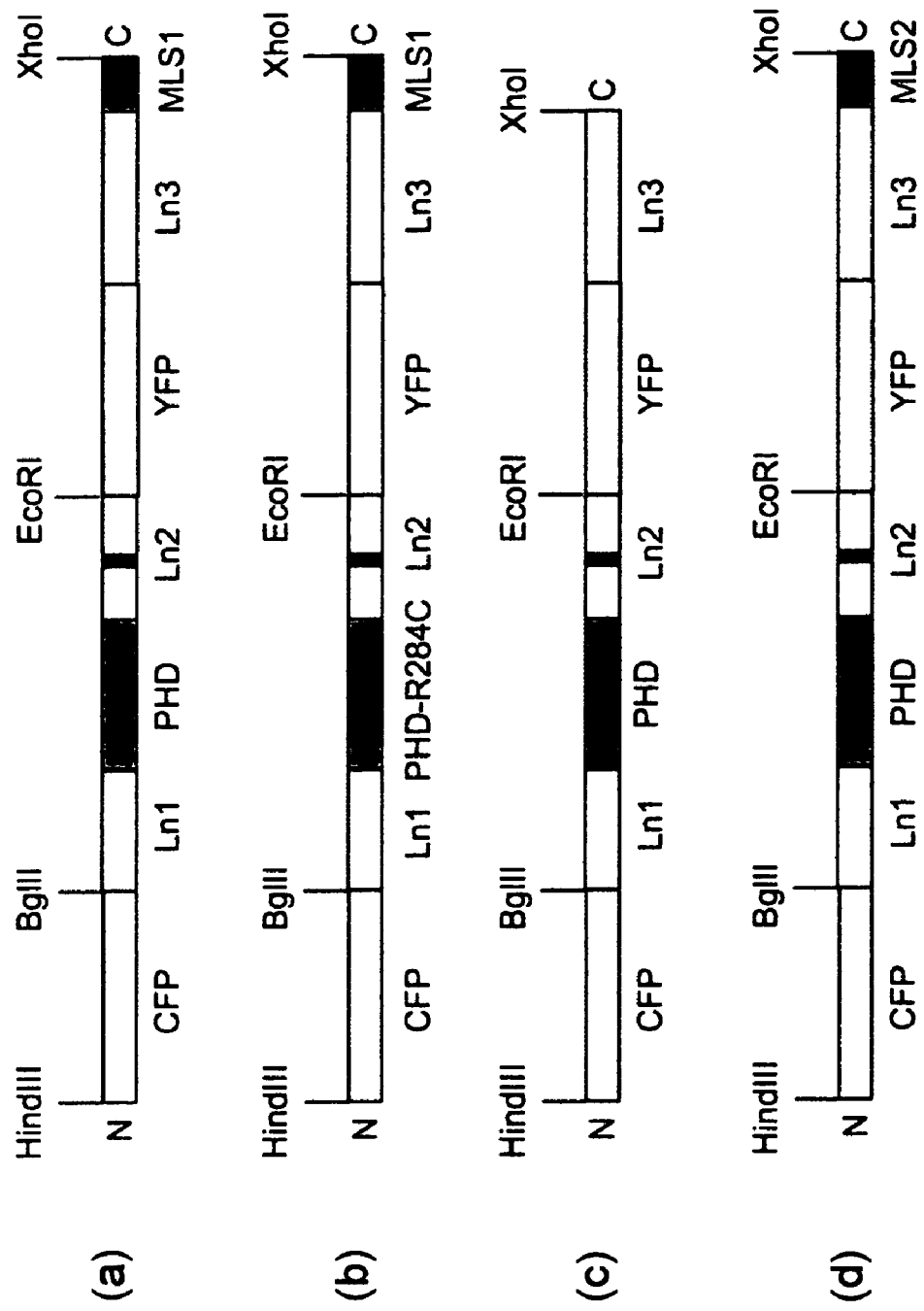
FIG. 2 is a schematic representation of domain structures of the probe for detecting and quantifying various kinds of lipid second messengers prepared in Examples of this invention (a: Fllip-pm; b: Fllip-pmR284C; c: Fllip-del; d: Fllip-em).

For probe 1, addition to Fllip-pm that has the full length of amino acid sequence of PHD (FIG. 2*a*), the followings were prepared by the same manner: a probe in which the 284th arginine residue of PHD was replaced with cysteine, abolishing binding to $PIP_3$ (hereinafter, referred to as "Fllip-pmR284C") (FIG. 2*b*); a probe having no membrane localization sequence MLS1 (hereinafter, referred to as "Fllip-del") (FIG. 2*c*); and a probe where membrane localization sequence MLS1 was changed to MLS2 (SEQ ID NO: 6) (hereinafter, referred to as "Fllip-em") (FIG. 2*d*).

Example 2

Introduction of the Probe into CHO-PDGFR Cells

Ovarian cells of Chinese hamster (CHO) were cultured in Ham's F-12 medium supplemented with 10% fetal calf serum (FCS) at 37° C. in 5% $CO_2$. The resulting CHO-PDGFR cells were plated onto glass-bottomed dishes, each of Fllip-pm, Fllip-pmR284C, Fllip-del and Fllip-em expression vectors were transfected with LipofectAMINE2000 reagent (manufactured by Life Technology) and left for 24 hours at 37° C. in 5% $CO_2$.

Example 3

Imaging of CHO-PDGFR with the Probe (1) Fllip-pm

After serum starvation with serum-free incubating medium, the medium was replaced with a Hank's balanced salt solution. Then, in accordance with a method already reported by the inventors (such as Non-Patent Documents 12 and 13), the cells were imaged at room temperature on a Carl Zeiss Axiovert 135 microscope with a cooled CCD camera, MicroMAX (Roper Scientific lnc, Tucson, Ariz.), controlled by MetaFluor. (Universal Imaging, West Chester, Pa.). The fluorescence images were obtained through 480±15 nm and 535±12.5 nm filters with a 40× oil immersion objective (Carl Zeiss, Jena, Germany). YFP images were detected by a confocal laser scanning microscope LSM 510 (Carl Zeiss).

Figure 3:
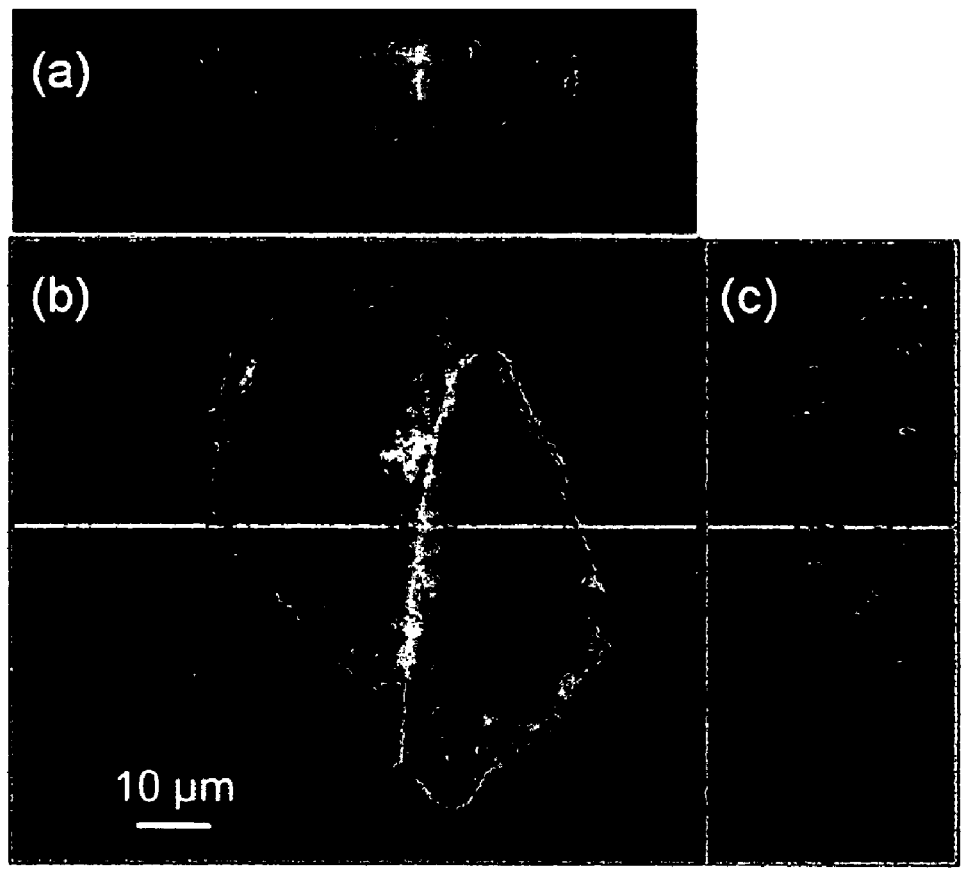
FIG. 3 is fluorescence microscopic images of Fllip-pm expressed in CHO cells in the Example of this invention (a and c: vertical direction; b: horizontal direction).

FIG. 3 is a microscopic image of Fllip-pm in CHO cells (a and c: vertical section; b: horizontal section). It was confirmed that Fllip-pm was mainly localized on plasma membrane of CHO-PDGFR cells.

(2) Fllip-em

Figure 4:
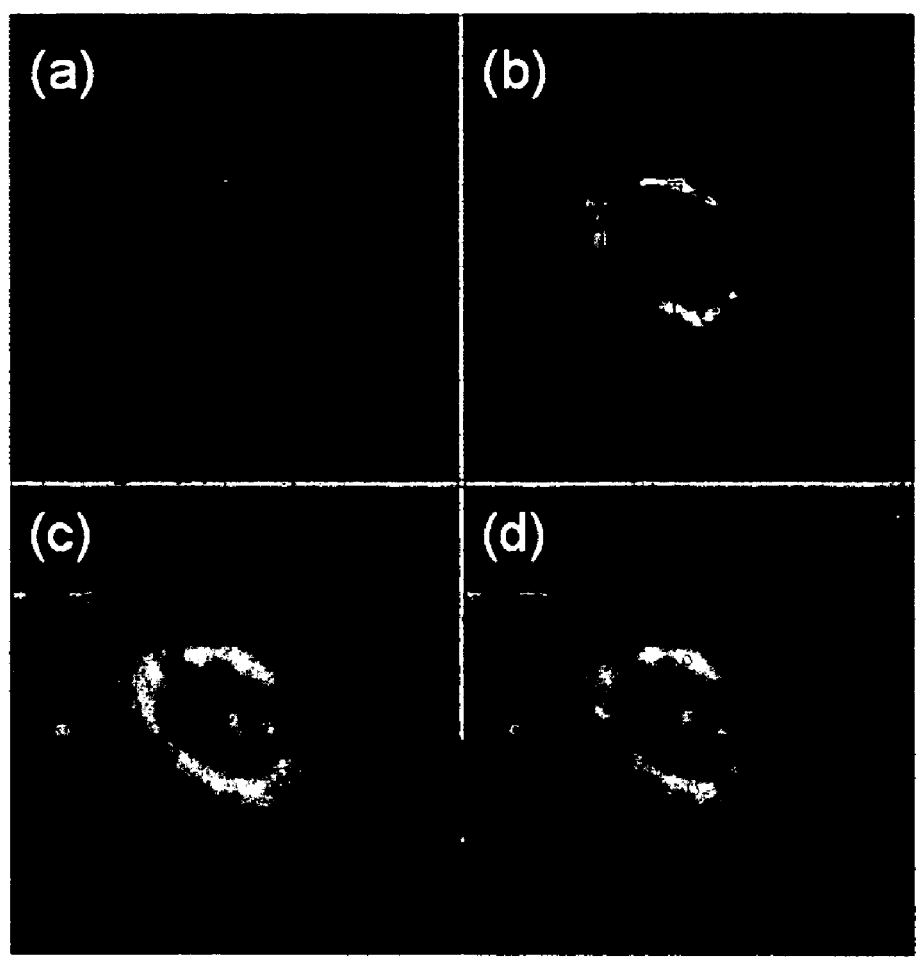
FIG. 4 confocal laser scanning microscopic images of Fllip-em expressed in CHO cells in the Example of this invention (a: stained with Cy5 by anti-GFP antibody; b: stained with BODIPY-ceramide CS which is a Golgi body marker; c: stained with breferdin A which is a endoplasmnic reticulum marker; d: superimposition of a, b and c).

A microscopic image of Fllip-em in CHO cells is shown in FIG. 4. a: Cy5 staining with anti-GFP antibody; b: BODIPY-ceramide C5 (the Golgi marker) staing; c: the breferdin A (the endoplasmic reticulum marker) staining; d: the merged image of a through c.

In Fllip-em, in which Cys 181 in MLS1 was replaced with a serine, the observed fluorescence was localized on the endomembranes (that is, the endoplasmic reticulum (ER) and Golgi apparatus.

Example 4

Response of the Probe (Addition of Synthetic $PIP_3$ into Fllip-pm-expressing CHO cells)

Each probe prepared in Example 1 was stimulated by microinjecting synthetic $PIP_3$ (1 µM) and fluorescence was measured by a dual-emission fluorescence microscope.

Figure 5:
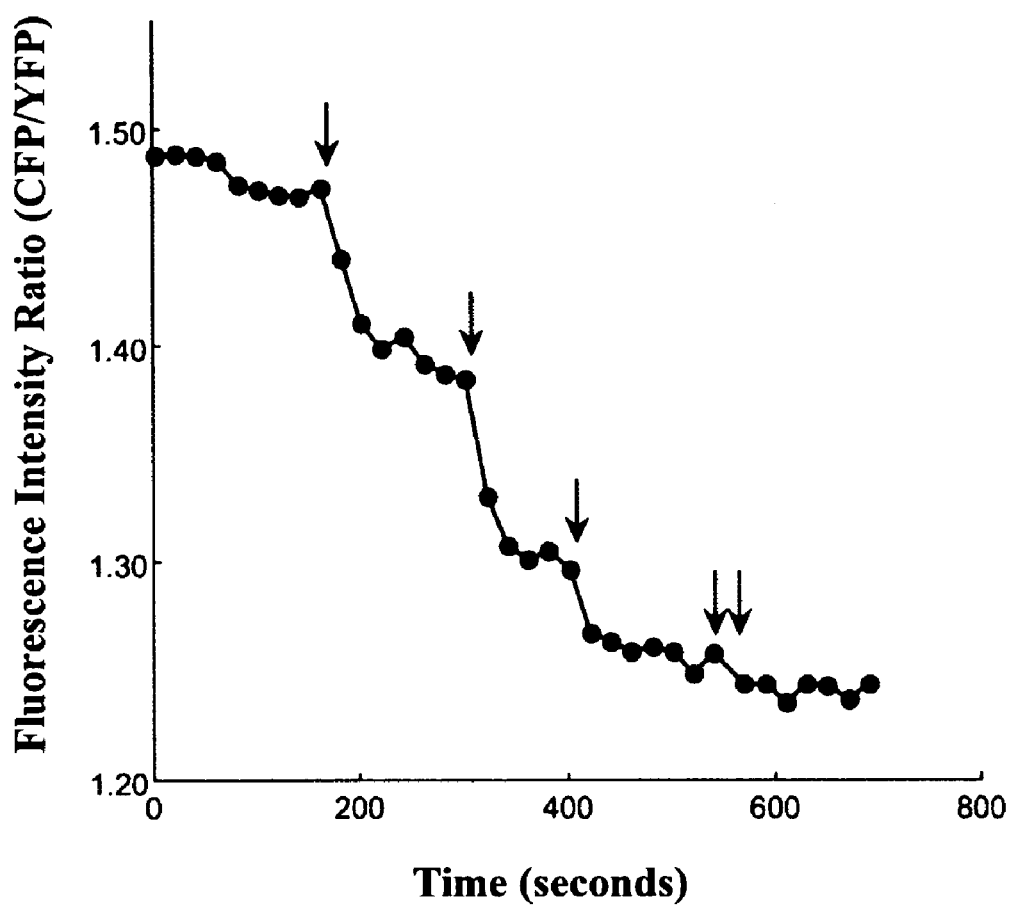
FIG. 5 is a graph showing the time course of FRET response of Fllip-pm in CHO cells (ratio of degree of CFP (480 ±15 nm) excited at 25° C. and 440 ±10 nm to emission intensity of YFP (535 ±12.5 nm) in the Example of this invention (Each arrow means addition of $PIP_3$ (1 µM)).

FIG. 5 shows the time course in FRET response of Fllip-pm in CHO cells. That is, it shows the emission ratio of CFP (480±15 nm) to YFP (535±12.5 nm) when excited at 440±10 nm at 25° C.

It was confirmed from FIG. 5 that the CFP:YFP emission ratio of Fllip-pm rapidly decreased by addition of synthetic $PIP_3$ (1 µM) and reached a plateau. Therefore, it was noted that FRET from CFP to YFP dependently increased on $PIP_3$, and Fllip-pm could be used for visualizing $PIP_3$ dynamic on plasma membrane.

Example 5

Response of the Probe (PDGF Stimulation to Fllip-pm-Expressing CHO-PDGFR Cells)

Response of Fllip-pm to $PIP_3$ produced by physiological stimulation was examined.

Fllip-pm was expressed in CHO-PDGFR cells stably expressing platelet-derived growth factor receptor (PDGFR). PDGF treatment promotes dimerization of PDGFR that results in phosphorylation of multiple tyrosine residues of PDGFR and its activation. PI3K is recruited to these tyrosine phosphorylation sites through its Src-homology 2 (SH2) domain, resulting in its activation (Schlessinger, J. (2000), *Cell*, 103, 211-225).

Figure 6:
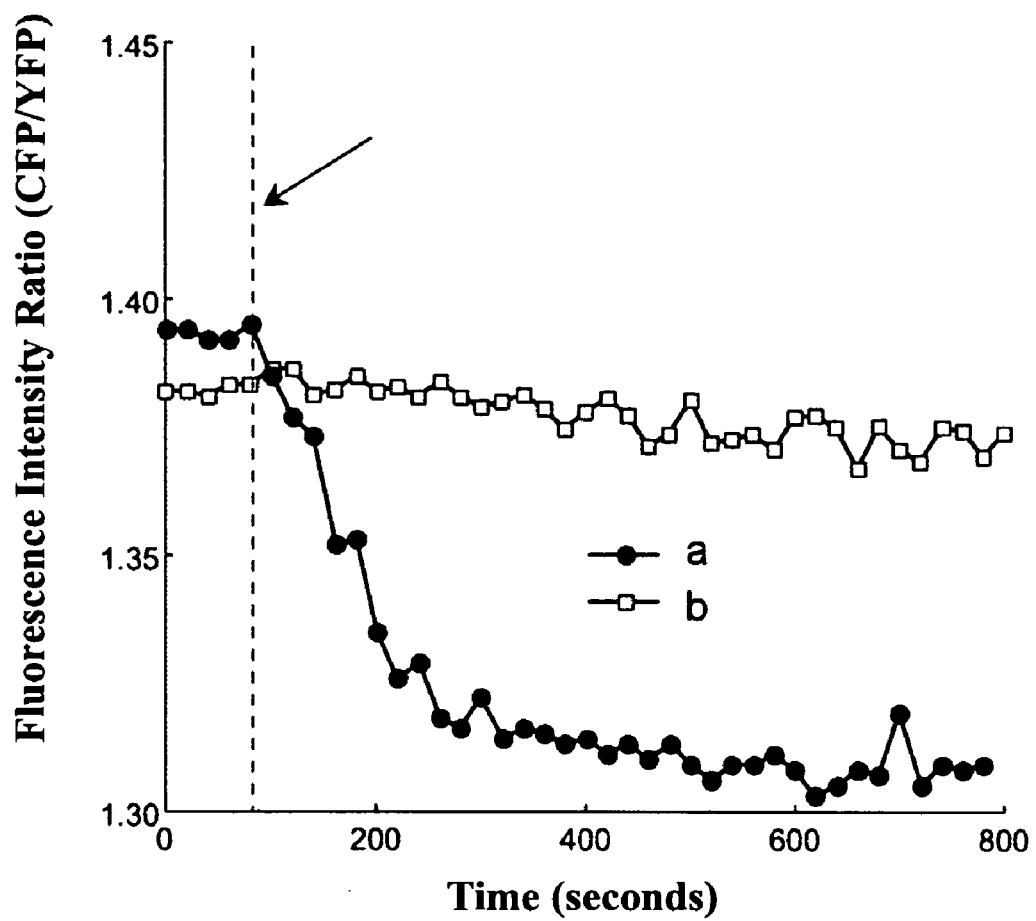
FIG. 6 is a graph showing the time course of CFP/YFP emission ratio when PDGF (50 ng/mL) was added to Fllip-pm-expressing CHO-PDGFR cells in the Example of this invention (Arrow/broken line: PDGF (50 ng/mL) added; a: PDGF added; b: PDGF added after Wortmannin treatment).
Figure 7:
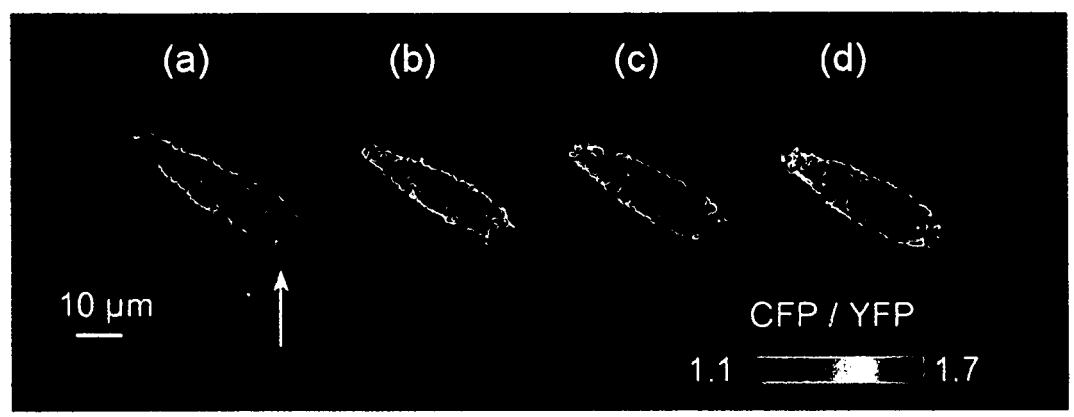
FIG. 7 is fluorescence microscopic images of Fllip-pm-expressing CHO-PDGFR cells before and after addition of PDGF (50 ng/mL) to the cells in the Example of this invention (a: 0 second; b: 100 seconds; c: 300 seconds: d: 500 seconds).

The time course of CFP/YFP-emission ratio when PDGF (50 ng/mL) was added to a cell expressing Fllip-pm at plasma membrane are shown in FIG. 6 and FIG. 7.

From FIG. 6a, it was confirmed that, as a result of addition of PDGF (50 ng/mL), the CFP/YFP emission ratio decreased immediately, reaching a plateau in 300 seconds.

On the other hand, the same pretreatment of the cell with 100 nM of wortmannin, which is a specific PI3K inhibitor, FRET response from Fllip-pm by the PDGF stimulation completely disappeared (FIG. 6b).

From the above, it was confirmed that Fllip-pm was able to detect the level of $PIP_3$ physiologically produced at plasma membrane.

Comparative Example 1

Response of the Probe (1) PDGF Stimulation in CHO-PDGFR Cell Expressing Fllip-pmR284C According to the same method as in Examples 4 and 5, response of Fllip-pmR284C, of which PHD was mutated not to bind to $PIP_3$, was examined.

Figure 8:
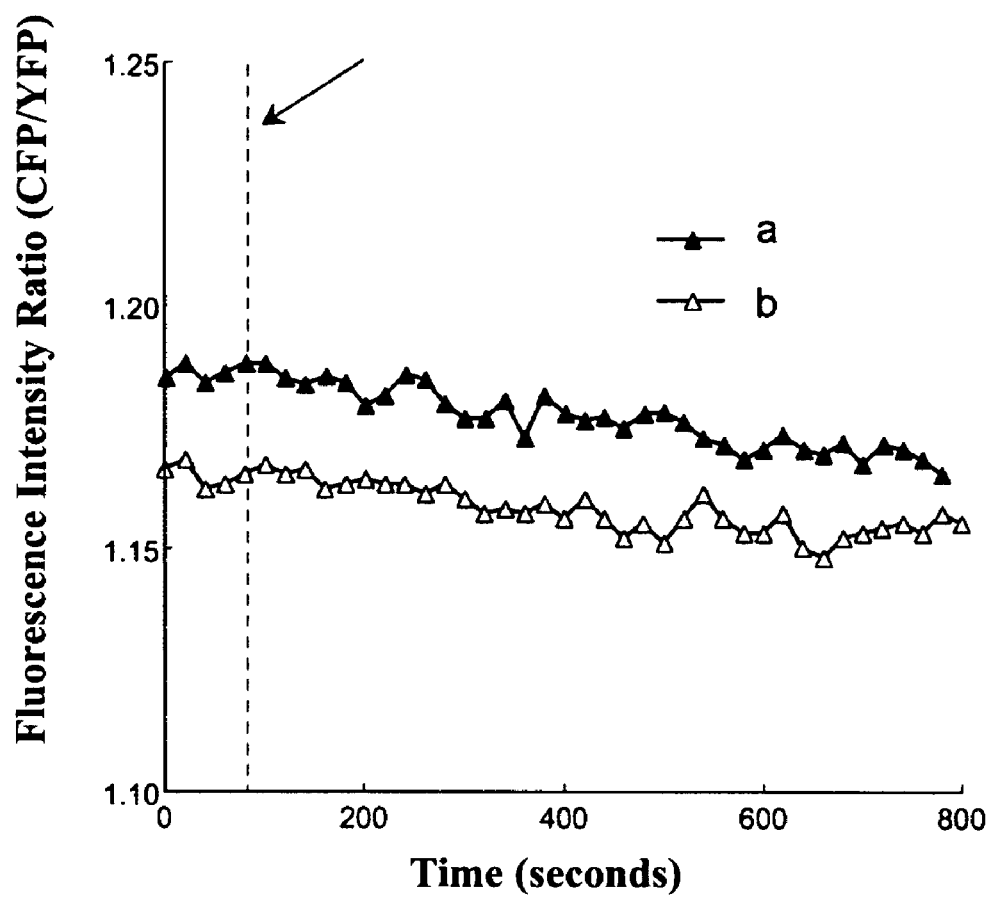
FIG. 8 is a graph showing the time course of CFP/YFP emission ratio when PDGF (50 ng/mL) was added to Fllip-pmR284C-expressing CHO-PDGFR cells and Fllip-del-expressing CHO-PDGFR cells in the Example of this invention (arrow/broken line: PDGF (50 ng/mL) added; a: Fllip-pmR284C; b: Fllip-del).

FIG. 8a shows the time course of CFR/YFP emission ratio when PDGF (50 ng/mL) was added to a cell expressing Fllip-pmR284C (FIG. 2b) at plasma membrane.

As mentioned in a publication (Venkateswarlu, K., Cunn-Moore, F., Tavare, J. M. and Cullen, P. J. (1999) *J. Cell Sci.*, 112, 1957-1965), Fllip-pmR284C did not respond to PDGF stimulation. Accordingly, it was confirmed that FRET response from Fllip-pm was caused by the fact that PHD recognized $PIP_3$ at membrane.

(2) PDGF Stimulation in CHO-PDGFR Cell Expressing Fllip-del

The time course of CFP/YFP emission ratio when PDGF (50 ng/mL) was added to a cell expressing Fllip-del lacking the membrane localization sequence (MLS) (FIG. 2d) at plasma membrane are shown in FIG. 8b.

Fllip-del did not show any response after PDGF stimulation.

Accordingly, it was confirmed that MLS is important not only for tethering the probe to cell membrane but also for eliciting a reversed type conformational change of the probe at membrane.

Example 6

Response of the Probe (PDGF Stimulation to Fllip-em-Expressing CHO-PDGFR Cells)

$PIP_3$ dynamics in the endomembranes, i.e., the endoplasmic reticulum and Golgi body, were visualized by using Fllip-em, location of which was shown to be spatially confirmed in endomembranes in Example 3(2).

Figure 9:
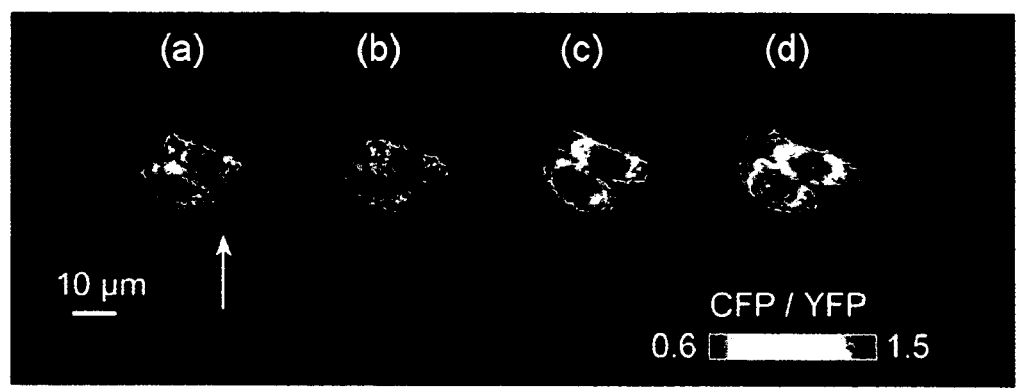
FIG. 9 is fluorescence microscopic images (25° C.) of Fllip-em-expressing CHO-PDGFR cells before and after addition of PDGF (50 ng/mL) to the cells in the Example of this invention (a: 0 second; b: 120 seconds; c: 300 seconds: d: 600 seconds).
Figure 10:
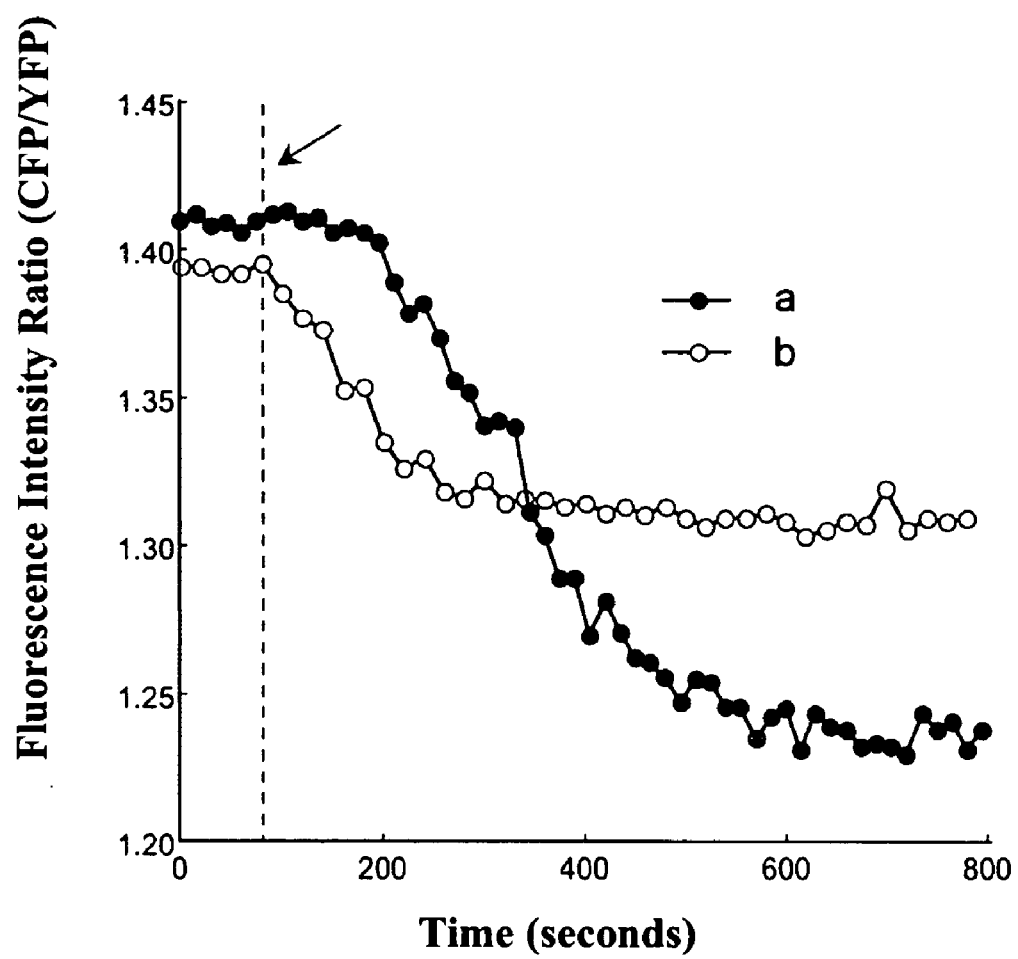
FIG. 10 is a graph showing the time course of CFR/YFP emission ratio when PDGF (50 ng/mL) was added to Fllip-em-expressing CHO-PDGFR cells and Fllip-pm-expressing CHO-PDGFR cells in the Example of this invention (arrow/broken line: PDGF (50 ng/mL) added; a: Fllip-em; b: Fllip-pm).

Fllip-em was expressed in the CHO-PDGFR cells by the same method as in Example 2. After that, the cells were stimulated with PDGF by the same method as in Example 5 and the time course of CFP/YFP emission ratio was measured. The result is shown in FIG. 9 and FIG. 10.

Upon PDGF stimulation, the CFP/YFP emission ratio of Fllip-em did not change immediately (FIG. 10a). On the other hand, Fllip-pm at the plasma membrane responded rapidly (FIG. 10b). However, after 100 to 150 seconds, the CFP/YFP emission ratio was found to decrease in the endomembranes and reach to a plateau in 500 seconds (FIG. 3a).

This result clearly indicates that $PIP_3$ is increased not only in the plasma membrane but also in encomembranes upon PDGF stimulation. Also, it should be noted that the extent of $PIP_3$ increase in the endomembranes was found to be twice to three times lager than that in the plasma membrane.

Incidentally, the present inventors have also confirmed that other peptide ligand, insulin and epidermal growth factors, likewise induced the $PIP_3$ increase in plasma membranes and endomembranes.

Example 7

To explore the molecular mechanism, which underlies the $PIP_3$ increase in the endomembranes, the effect on the $PIP_3$ increase of a dominant-negative mutant of dynamin (DynK44A), in which the lysine 44 is substituted by an alanine, was assessed.

The dynamin is a guanosine triphosphatase (GTPase) that controls the clathrin-mediated endocytosis (Qualmann, B., Kessels, M. M. and Kelly, R. B. (2000) *J. Cell Biol.*, 150, F111-F116) of receptor tyrosine kinases, including PDGFR. DynK44A lacks the GTPase activity and inhibits a clathrin-mediated endocytosis of PDGFR.

Figure 11:
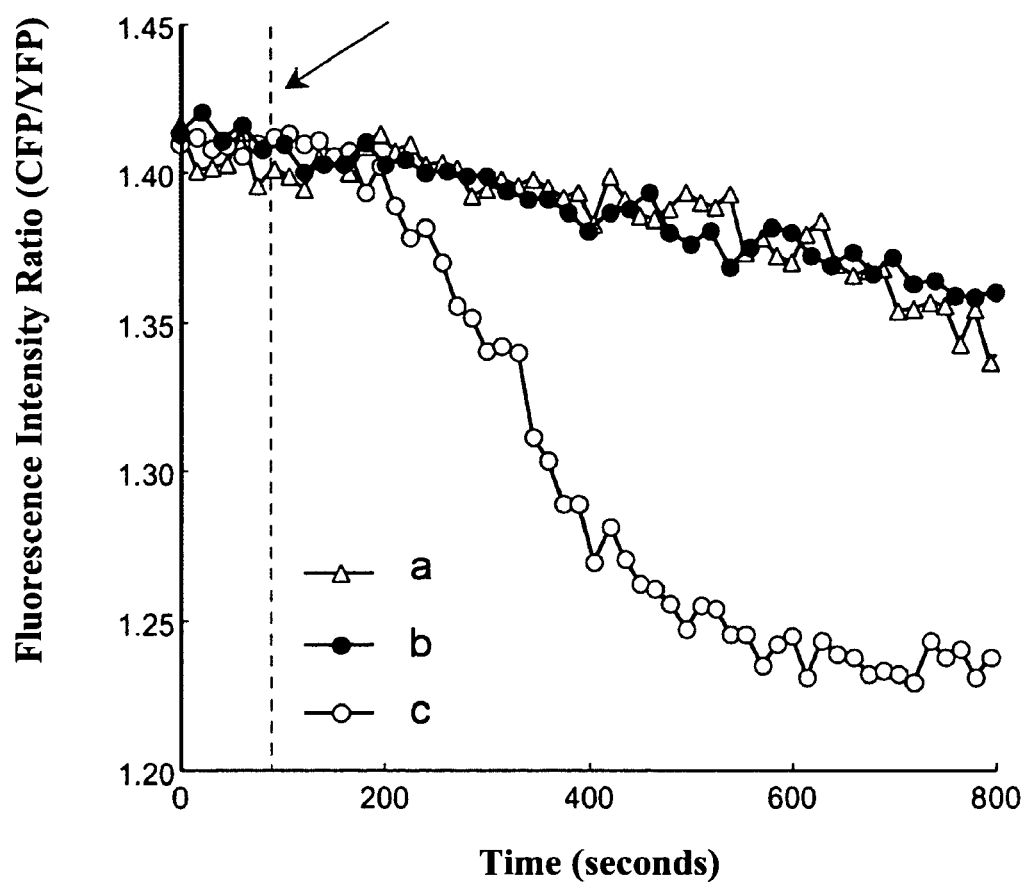
FIG. 11 is a graph showing the time course of CFP/YFP emission ratio at endomembranes when DynK44A-expressing CHO-PDGFR cells were stimulated with PDGF (50 ng/mL) in the Example of this invention (arrow/broken line: PDGF (50 ng/mL) added; a: no expression of DynK44A (endoplasmic reticulum stimulation); b: expression of DynK44A (PDGF stimulation); c: no expression of DynK44A (PDGF stimulation)).
Figure 12:
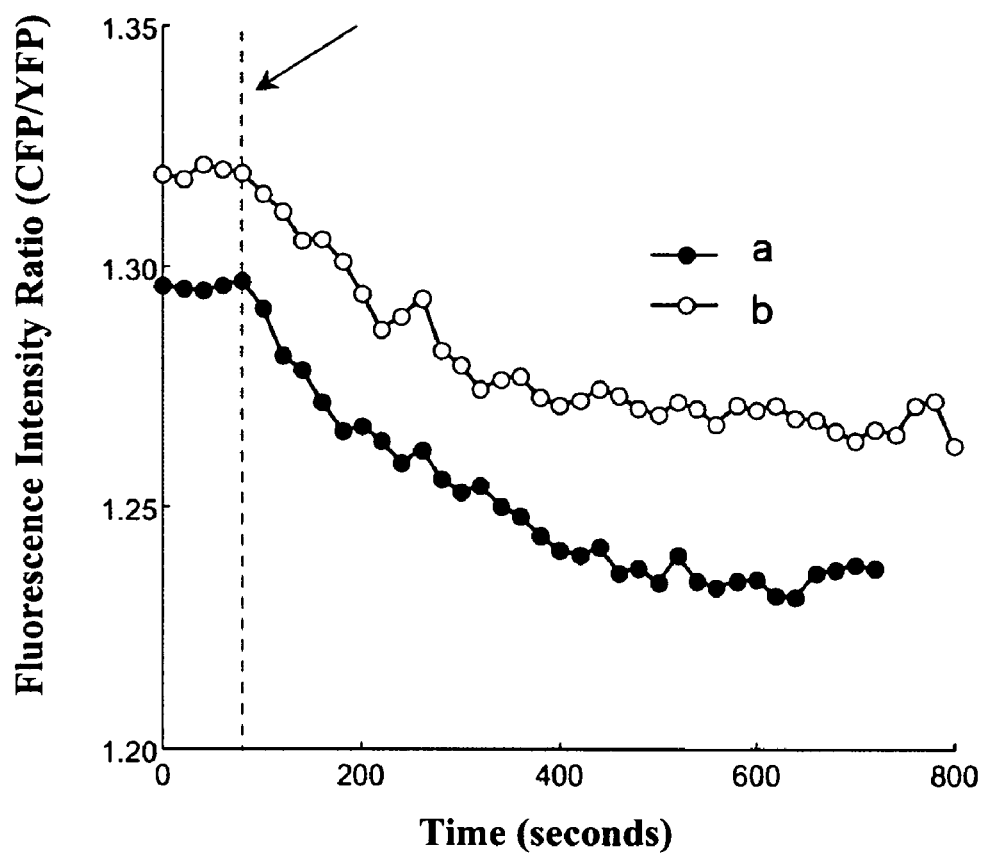
FIG. 12 is a graph showing the time course of CFP/YFP emission ratio at the plasma membrane when DynK44A-expressing CHO-PDGFR cells were stimulated with PDGF (50 ng/mL) in the Example of this invention (arrow/broken line: PDGF (50 ng/mL) added; a: expression of DynK44A; b: no expression of DynK44A).

The DynK44A was expressed in CHO-PDCFR cells by adenovirus-mediated gene transfer, the cells were stimulated with PDGF (50 ng/mL) and time course of CFP/YFP in endomembranes was measured as shown in FIG. 11. The FRET response was completely lost to the basal level in the endomembranes. On the other hand, in the plasma membrane, the FRET response of Fllip-pm was immediately observed upon PDGF stimulation even in the presence of the DynK44A expression, as observed in the absence of the DynK44A expression (FIG. 12).

These results show that the PDGF-stimulated $PIP_3$ increase in the endomembranes was completely inhibited by overexpression of the DynK44A, whereas that in the plasma membrane was not affected. The $PIP_3$ increase in the endomembranes by other peptide ligands, insulin and epidermal growth factor, was also inhibited by the DynK44A overexpression. Thus, it was revealed that the clathrin-mediated endocytosis causes the time-delayed $PIP_3$ increase in the endomembranes.

Example 8

It was investigated how the endocytosis triggers the $PIP_3$ increase in the endomembranes.

For further dissecting the $PIP_3$ dynamics in the endomembranes, protein tyrosine phosphatase-1B (PTP1B) was overexpressed in CHO-PDGFR cells by adenovirus-mediated gene transfer. The PTP1B is localized exclusively on the cytoplasmic surface of the ER (Frangioni, J. V., Beaham, P. H., Shifrin, V., Jost, C. A. and Neel, B. G. (1992) *Cell*, 68, 545-560). It has recently been reported that upon ligand stimulations, receptor tyrosine kinases, including PDGFR, are dephosphorylated and inactivated by the PTP1B on the cytoplasmic surface of the ER after the receptors activated at the cell surface were internalized by endocytosis (Haj, F. G., Verveer, P. J., Squire, A., Neel, B. G. and Bastiaens, P. I. H. (2002), *Science*, 295, 1708-1711).

The inventors expected the overexpressed PTP1B to selectively dephosphorylate the endocytosed PDGFR and to inhibit the recruitment and activation of PI3K by the PDGFR on the cytoplasmic surface of ER, without affecting the PDCFR in the plasma membrane.

Figure 13:
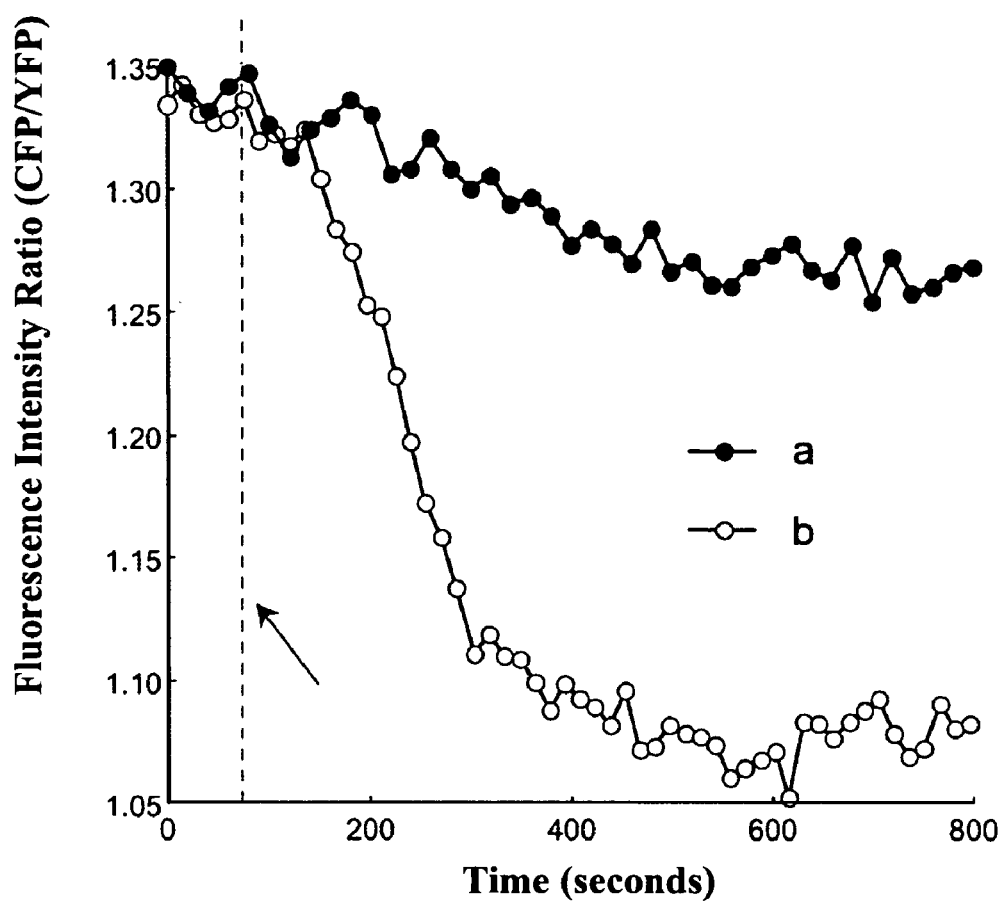
FIG. 13 is a graph showing the time course of CFP/YFP emission intensity ratio at endomembranes when PDGF was added to CHO-PDGFR cells where PTP1B was excessively expressed using Fllip-em in the Example of this invention (arrow/broken line: PDGF (50 ng/mL) added; a: excessive expression of PTP1B; b: no excessive expression of PTP1B).

PTP1B was overexpressed in CHO-PDGFR cells and time course of CYP/YFP emission ratio in endomembranes after PDGF stimulation using Fllip-em were measured as shown in FIG. 13 the PDGF-stimulated $PIP_3$ increase was completely lost.

Figure 14:
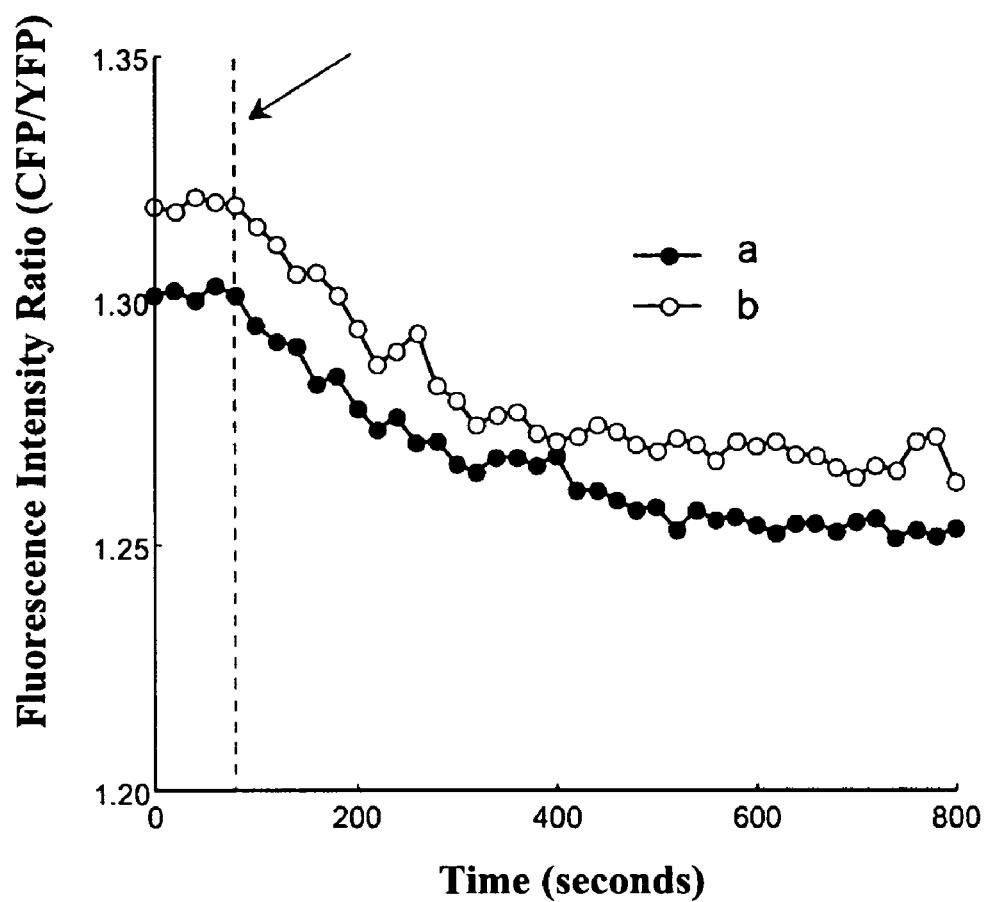
FIG. 14 is a graph showing the time course of CFP/YFP emission intensity ratio at the plasma membrane when PDGF was added to CHO-PDGFR cells where PTP1B was excessively expressed using Fllip-em in the Example of this invention (arrow/broken line: PDGF (50 ng/mL) added; a: excessive expression of PTP1B; b: no excessive expression of PTP1B).

On the other hand, in the plasma membrane, the $PIP_3$ increases upon PDGF stimulation, which was monitored with Fllip-pm, was not affected by the overexpression of PTP1B (FIG. 14). It is probably due to the absence of PTP1B in the plasma membrane.

Taken these together, it is concluded that $PIP_3$ was increased by its production in the endomembranes when the activated PDGFR was internalized to the endomembranes by the clathrin-coated endocytosis vesicles and thereby activated the P13K there. This means that the influx by the endocytosis vesicles of the $PIP_3$ produced in the plasma membrane to the endomembranes is negligible, but rather that the $PIP_3$ observed in the endomembranes is produced in situ in the endomembranes.

Example 9

It has been known that C1B domain derived from PKC is selectively bound to DAG. Therefore, this domain was selected as an LBD and the lipid second messenger detecting- and quantifying-probe (hereinafter, referred to as DAG-Fllip) was prepared. Localization domains to the plasma membrane and endomembranes are linked with DAG-fllip to prepare DAG-fllip-pm and DAG-fllip-em. After that, in order to confirm whether the DAG-fllip-pm and the DAG-fllip-em respond to DAG, the DAG-fllip-pm and the DAG-fllip-em were evaluated by using phorbol ester (PMA), which is a substance having a membrane permeability, and specifically bound to C1B domain.

Figure 15:
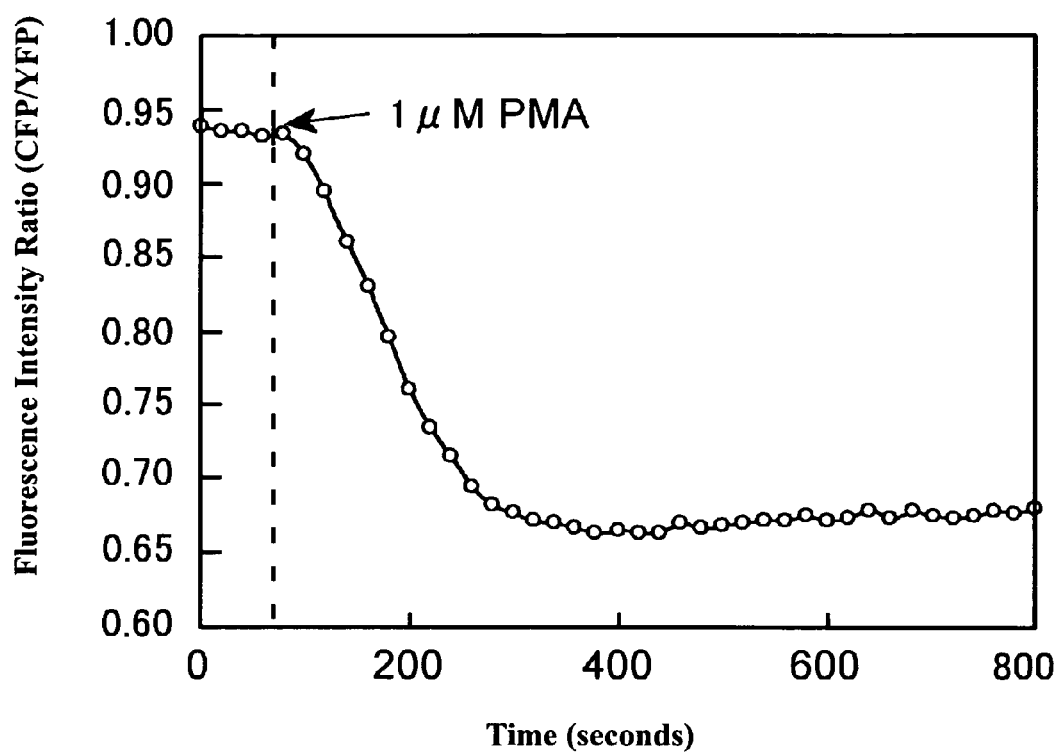
FIG. 15 is a graph showing the time course of CFP/YEF emission intensity ratio when PMA was added to DAG-flip-pm and DAG-flip-em in the Example of this invention.

When phorbol ester was added, fluorescence intensity ratios were decreased in both cases of fllip-pm and fllip-em (FIG. 15).

From this result, it was confirmed that each of the DAG-fllip-pm and DAG-fllip-em acts as probes for visualizing DAG in cell membrane and endomembranes.

INDUSTRIAL APPLICABILITY

As fully illustrated hereinabove, this invention provides a probe by which a lipid second messenger can be detected and quantified easily with high accuracy even in vivo, and also provides a method for detecting and quantifying a lipid second messenger using the probe. The probe of this invention is genetically encoded fluorescent indicators and has general applicability for other lipid second messengers as well.

Accordingly, when the probe of this invention is used, it is now possible to visualize not only the dynamics of lipid second messengers in a single living cell but also in which of plasma membrane and endomembranes a lipid second messenger is increased by various stimulations from outside or by what mechanism a lipid second messenger is increased is elucidated.

Receptor endocytosis has previously been suggested to play roles not only in attenuating the receptor activation but also in modulating the downstream signaling (Vieria, A. V., Lamaze, C. and Schmid, S. L. (1996) *Science*, 274, 2086-2089; Ceresa, B. C. and Schmid, S. L. (2000) *Curr. Opin. Cell*

Biol., 12, 204-210; Lavoie, C. et al. (2002) *J. Biol. Chem.*, 277, 35402-35410). However, to date, it has not yet been clarified exactly how, when and where the signaling pathways are elicited by the receptor endocytosis in living cells. The probe of the invention is very highly useful in knowing wide insights into mechanism, timing and location of the lipid second messenger production.

In addition, by using the probe of this invention, it is expected to clarify that, for example, the same lipid second messenger (such as $PIP_3$) produced in different membrane in cells adjusts different downstream signal depending upon the type of the binding protein and finally leads to individual cell functions such as gene expression, cell metabolism and cell skeleton adjustment.

The invention claimed is:

1. A probe for detection and quantification of a lipid second messenger, which comprises:
   a polypeptide which can specifically bind the lipid second messenger,
   a first chromophore linked to one end of the polypeptide through a rigid linker sequence;
   a second chromophore linked to another end of the polypeptide through a second rigid linker sequence, wherein the second chromophore has a different fluorescence wavelength from the first chromophore, and the second linker sequence is rigid except for a single flexible site acting as a hinge; and
   a membrane localization sequence linked to the second chromophore through a third rigid linker sequence, wherein when the polypeptide is bound to the lipid second messenger, the first and second chromophores are capable of Fluorescence Resonance Energy Transfer (FRET).

2. The probe for detection and quantification of a lipid second messenger of claim 1, wherein the polypeptide which can specifically bind the lipid second messenger is a lipid second messenger-binding protein.

3. The probe for detection and quantification of a lipid second messenger of claim 2, wherein the lipid second messenger-binding protein is a pleckstrin homology domain from General Receptor for Phosphoinositides-1 (GRP 1).

4. The probe for detection and quantification of a lipid second messenger of claim 1, wherein the chromophores are a cyan fluorescent protein linked to N-terminal end of the polypeptide and a yellow fluorescent protein linked to C-terminal end of the polypeptide.

5. The probe for detection and quantification of a lipid second messenger of claim 1, wherein the first, second and third linker sequences comprise a rigid α-helix linker consisting of repeated sequences of SEQ ID NO: 1.

6. The probe for detection and quantification of a lipid second messenger of claim 1, wherein the single flexible site of the second linker sequence is a single di-glycine motif.

7. The probe for detection and quantification of a lipid second messenger of claim 1, wherein the membrane localization sequence is a lipidized sequence or a transmembrane sequence.

8. A method for detecting and quantifying a lipid second messenger, comprising:
   contacting the probe with the lipid second messenger of claim 1; and measuring changes in fluorescence spectra.

* * * * *